United States Patent [19]

DesMarais

[11] Patent Number: 5,352,711

[45] Date of Patent: Oct. 4, 1994

[54] METHOD FOR HYDROPHILIZING ABSORBENT FOAM MATERIALS

[75] Inventor: Thomas A. DesMarais, Norwood, Ohio

[73] Assignee: The Procter & Gamble Company, Cincinnati, Ohio

[21] Appl. No.: 743,951

[22] Filed: Aug. 12, 1991

[51] Int. Cl.⁵ .............................................. C08J 9/28
[52] U.S. Cl. ...................................... 521/149; 521/61; 521/63; 521/64; 521/88; 521/146; 521/150; 521/155; 524/801; 524/804
[58] Field of Search .............. 521/149, 88, 61, 63, 521/64, 146, 149, 150, 155; 524/801, 804

[56] References Cited

U.S. PATENT DOCUMENTS

| | | | |
|---|---|---|---|
| 3,255,127 | 6/1966 | von Bonin | 525/201 |
| 3,734,867 | 5/1973 | Will | 521/63 |
| 3,763,056 | 10/1973 | Will | 521/62 |
| 4,076,656 | 2/1978 | White et al. | 521/88 |
| 4,473,611 | 9/1984 | Haq | 428/198 |
| 4,522,953 | 6/1985 | Barby et al. | 521/64 |
| 4,606,958 | 8/1986 | Haq et al. | 428/198 |
| 4,611,014 | 9/1986 | Jomes et al. | 521/146 |
| 4,612,334 | 9/1986 | Jones et al. | 521/146 |
| 4,668,709 | 5/1987 | Jones et al. | 521/146 |
| 4,675,213 | 6/1987 | Yamamori | 521/149 |
| 4,788,225 | 11/1988 | Edwards et al. | 521/149 |
| 4,797,310 | 1/1989 | Barby et al. | 428/71 |
| 5,147,345 | 9/1992 | Young et al. | 428/286 |
| 5,149,720 | 9/1992 | DesMarais et al. | 521/64 |

FOREIGN PATENT DOCUMENTS 0299762 1/1989 European Pat. Off. .

*Primary Examiner*—John Kight, III
*Assistant Examiner*—John M. Cooney, Jr.
*Attorney, Agent, or Firm*—Eric W. Guttag

[57] ABSTRACT

Normally hydrophobic foams, such as polyurethane foams and polymerized water-in-oil emulsion foams, are rendered hydrophilic by means of treatment with simple surfactants and hydrophilizing agent salts. Thus, a surfactant-containing foam is treated with a solution of, for example, calcium chloride, and is dried to leave a substantially uniformly distributed residue of hydrated or hydratable calcium chloride on the surfactant-containing internal foam surfaces. In-use, the combination of surfactant and calcium chloride hydrate provides a hydrophilic surface to the foam. Other hydratable calcium or magnesium salts such as magnesium chloride can be used. The resulting hydrophilized foams are suitable for use in absorbent devices, including diapers, sanitary napkins, bandages, and the like.

20 Claims, 2 Drawing Sheets

|—|
0 10u

METHOD FOR HYDROPHILIZING ABSORBENT FOAM MATERIALS

FIELD OF THE INVENTION

The present invention relates to a method for converting normally hydrophobic polymeric foams into hydrophilic foams. The foams thus "hydrophilized" are suitable for use in absorbent devices such as diapers, adult incontinence garments, sanitary napkins, bandages, and the like, which are especially adapted for absorbing various aqueous bodily fluids.

BACKGROUND OF THE INVENTION

A wide variety of foam materials, or common "sponges", which effectively absorb moisture are well-known in commercial practice. Typically, such foams are open-cell structures and comprise various cellulosic or polymeric materials. For example, various polyurethanes and like materials have long been used to prepare synthetic foams. As is known in the art, foam materials function most efficiently as absorbents for aqueous liquids when their surfaces are substantially hydrophilic. However, many synthetic foams are prepared by the polymerization of organic monomers which yield polymeric foams which are substantially hydrophobic in nature. Accordingly, considerable attention has been given to finding means whereby otherwise hydrophobic synthetic foams can be rendered hydrophilic.

For example, it is known that some types of foams have been prepared using certain selected monomers which, themselves, impart at least some degree of hydrophilic character to the resulting polymerized foam. Such monomers are then incorporated into the basic structure of the foam network during the polymerization process. Unfortunately, the hydrophilic substituents present in the monomers can undesirably modify the basic characteristics of the resulting foam. Thus, while the resulting foam may have the desired hydrophilic character, it may lose some of its other desirable structural features or performance qualities. Moreover, such specialized, hydrophilic monomers can be expensive relative to standard monomers used to prepare foams, and thus their use can increase the overall cost of the foam.

In other processes, some foams have been treated to provide anionic substituent groups such as carboxylate or sulfonate moieties on their polymeric structures. Such anionic substituents can be effective in hydrophilizing the surface of the foams, but, unfortunately, their utilization can result in foams that are rather stiff and lack resilience. Such foams are not optimally comfortable when used in close contact with human skin, as, for example, in diapers and sanitary articles.

In some instances, synthetic hydrophobic foams can be rendered hydrophilic by incorporating small quantities of surfactants into the foam matrix. While this can render a foam hydrophilic and quite useful for some purposes, surfactant-containing foams are not always suitable for use in prolonged contact with skin, since the surfactant can cause skin irritation. In addition, some surfactants, e.g., water-soluble ones, can desorb from the foam and dissolve into the fluid being absorbed by the foam. This can significantly change the surface tension of the fluid and dramatically affect the strength with which it is held by the foam.

The manufacture of hydrophilic foams for use as fluid absorbents in sanitary articles, especially disposable diapers and sanitary napkins, requires that the foams not only have superior fluid-handling properties, but also be comfortable to the wearer and safe when used in close proximity to human skin over prolonged periods of wear. Moreover, it is important to the performance of foams designed for use in diapers and catamenials that the fluidity properties of body fluids such as urine and menses not be substantially affected by the hydrophilizing agent, such as could happen when some surfactants, e.g., water-soluble ones, are used to hydrophilize absorbent foams. Accordingly, safe, effective, economical means for hydrophilizing absorbent foams is of substantial interest to the manufacturer of such items. The present invention provides a safe and effective foam hydrophilization method which meets the foregoing requirements.

BACKGROUND ART

Lindquist; U.S. Pat. No. 3,563,243; Issued Feb. 16, 1971 relates to the use of oxyalkylene-substituted polyurethane foams in diapers. See also Kao; Japanese Patent Application 02-239863; Laid Open Sep. 21, 1990.

Jones et. al.; U.S. Pat. No. 4,612,334; Issued Sep. 16, 1986 and Haq et. al.; U.S. Pat. No. 4,606,958; Issued Aug. 19, 1986 both relate to certain foams having carboxy and other artionic substituent groups.

Unilever; EPO Patent Application 299762; Published Jan. 18, 1989 relates to the use of calcium chloride in the manufacture of high internal phase emulsion foams.

Kelly et. al.; U.S. Pat. No. 4,985,467; Issued Jan. 15, 1991 discloses a hydrophilic polyurethane foam comprising superabsorbent material. This patent also cites the following references relating to absorbent foams and/or other absorbent materials: U.S. Pat. Nos. 4,104,435; 4,717,738; 4,725,629; 4,076,663; 4,454,268; 4,337,181; 4,133,784; 3,669,103; 4,464,428; 4,394,930; 3,900,030; 4,239,043; 4,731,391 and Japanese 55-168104 (1982); 57-92032 (1982); also U.S. Pat. Nos. 3,021,290; 3,171,820; 3,175,025; 4,359,558; and 4,521,544.

Barby et. al.; U.S. Pat. No. 4,797,310; Issued Jan. 10, 1989; Edwards et. al.; U.S. Pat. No. 4,788,225; Issued Nov. 29, 1988 and Barby et. al.; U.S. Pat. No. 4,522,953; Issued Jun. 11, 1985 all relate to porous polymeric materials (foams), some of which contain surfactants and which presumably are hydrophilic.

SUMMARY OF THE INVENTION

The present invention provides a method for rendering substantially hydrophobic polymeric foams suitable for absorbing hydrophilic liquids. In the first step of such a method, both a certain type of surfactant and a solution formed from a solvent such as water and a certain type of hydrophilizing agent salt are incorporated into a polymeric foam material which is substantially hydrophobic in the absence of added or residual hydrophilizing agents. In a second step of the method herein, this treated polymeric foam material is dried to remove solvent therefrom and to thereby leave incorporated within the foam material a substantially uniformly distributed, hydrophilizing amount of both the surfactant and the hydrophilizing agent salt. The surfactant which is employed is one which is substantially water-insoluble and is mild and relatively non-irritating to the skin. The specific hydrophilizing agent salts which are essentially employed in this method are the toxicologically acceptable, hydrated or hydratable calcium and magnesium salts such as calcium chloride and magnesium chloride.

The present invention is also directed to hydrophilized polymeric foam materials themselves which are suitable for absorbing hydrophilic liquids. Such foams have the above mentioned surfactants and hydrophilizing agent salts incorporated therein in substantially uniformly distributed, hydrophilizing amounts comprising at least about 0.05% by weight of the foam. Such foams furthermore contain no more than about 50% by weight of the foam of free water.

DETAILED DESCRIPTION OF THE INVENTION

Figure 1:
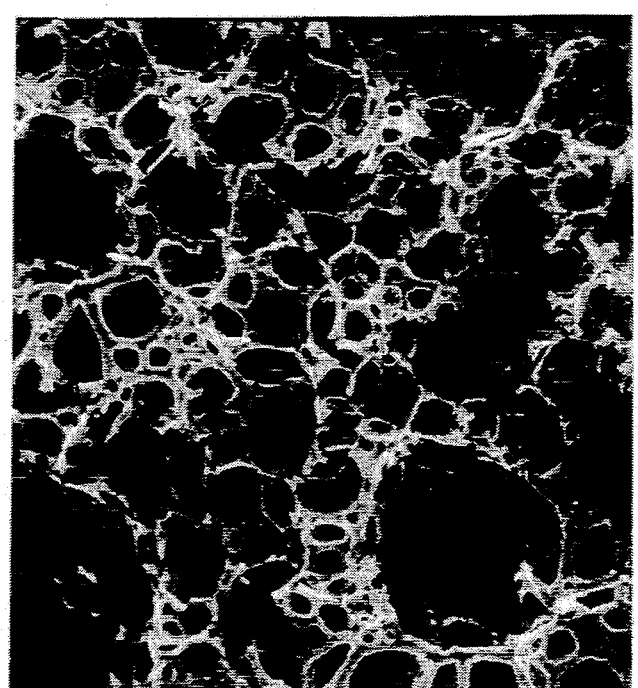
FIG. 1 of the drawings is a photomicrograph of the interstices of a typical hydrophilizable absorbent foam of the present invention.

The hydrophilization method of the present invention deals with the treatment of polymeric foam materials which are suitable for absorbing liquids into their foam structures. Polymeric foams can in general be characterized as the structures which result when a relatively monomer-free gas or relatively monomer-free liquid is dispersed as bubbles in a polymerizable monomer-containing liquid, followed by polymerization of the polymerizable monomers in the monomer-containing liquid which surrounds the bubbles. The resulting polymerized dispersion can be in the form of a porous solidified structure which is an aggregate of cells, the boundaries or walls of which cells comprise solid polymerized material. The cells themselves contain the relatively toohomer-free gas or relatively toohomer-free liquid which, prior to polymerization, had formed the "bubbles" in the liquid dispersion.

As described more fully hereafter, preferred polymeric foam materials useful in the present invention are those prepared by polymerizing a particular type of water-in-oil emulsion. Such an emulsion is formed from a relatively small amount of a polymerizable monomer-containing oil phase and a relatively larger amount of a relatively toohomer-free water phase. The relatively monomer-free, discontinuous "internal" water phase thus forms the dispersed "bubbles" surrounded by the continuous polymerizable monomer-containing oil phase. Subsequent polymerization of the monomers in the continuous oil phase forms the cellular foam structure. The aqueous liquid remaining in the foam structure formed upon polymerization can be removed by pressing and/or drying the foam.

Highly preferred polymeric foam materials for use in the present invention are those prepared by polymerizing water-in-oil emulsions containing certain polymerizable monomers, such as styrene, alkyl(meth)acrylates and/or divinylbenzene, in the oil phase of such emulsions. The most preferred polymeric foam materials of this type are those described in the concurrently filed patent application of DesMarais, Stone, Thompson, Young, LaVon, and Dyer having U.S. application Ser. No. 07/743,839, U.S. Pat. No. 5,260,345 entitled "Absorbent Foam Materials for Aqueous Body Fluids and Absorbent Articles Containing Such Materials," which application is incorporated herein by reference. Such highly preferred foam materials will generally have a pore volume of from about 12 to 100 ml/g and a capillary suction specific surface area of from about 0.5 to 5.0 m$^2$/g. These foams can be prepared from water-in-oil emulsions wherein the water to oil weight ratio ranges from about 12:1 to 100:1, more preferably from about 20:1 to 70:1.

Another common type of polymeric foam material useful in the present invention comprises the polyurethanes. Polyurethane foams are those prepared by reacting a polyisocyanate such as a diisocyanate with a hydroxyl-containing material such as a polyether polyol in the presence of water and a catalyst. As the polymer forms, the water reacts with the isocyanate groups to cause crosslinking. Carbon dioxide is also produced, and this causes foaming. Trifluoromethane or other volatile materials may also be employed as a blowing agent.

Polymeric foams, including the preferred foams herein prepared from polymerizable water-in-oil emulsions, may be relatively closed-celled or relatively open-celled in character, depending upon whether and/or the extent to which, the cell walls or boundaries, i.e., the cell windows, are filled or taken up with polymeric material. The polymeric foam materials useful in the method of the present invention are those which are relatively open-celled in that the individual cells of the foam are for the most part not completely isolated from each other by polymeric material of the cell walls. Thus the cells in such substantially open-celled foam structures have intercellular openings or "windows" which are large enough to permit ready fluid transfer from one cell to the other within the foam structure.

In substantially open-celled structures of the type useful herein, the foam will generally have a reticulated character with the individual cells being defined by a plurality of mutually connected, three dimensionally branched webs. The strands of polymeric material which make up the branched webs of the open-cell foam structure can be referred to as "struts." Open-celled foams having a typical strut-type structure are shown by way of example in the photomicrograph set forth as FIG. 1. For purposes of the present invention, a foam material is "open-celled" if at least 80% of the cells in the foam structure are in fluid communication with at least one adjacent cell.

The polymeric materials that form the foams which are used as the starting materials in the method of this invention will generally be non-swellable in aqueous liquids and will also generally be substantially free of polar functional groups on their polymer structures. Thus after the structures of such foams have been formed, the foam structure surfaces comprise polymeric materials which, in the absence of any residual or added surfactants or other hydrophilizing agents, would be substantially hydrophobic in character.

The extent to which polymeric foam materials are either "hydrophobic" or "hydrophilic" can be quantified by referencing the "adhesion tension" exhibited by such foams in contact with an absorbable test liquid. Adhesion tension is defined by the formula $$AT = \gamma \cos\theta$$

wherein

AT is adhesion tension in dynes/cm;

γ is the surface tension of a test liquid absorbed by the foam material in dynes/cm;

θ is the contact angle in degrees between the surface of foam polymer material and the vector which is tangent to the test liquid at the point that the test liquid contacts the foam polymer surface.

For any given foam material, the adhesion tension exhibited by the foam can be determined experimentally using a procedure whereby weight uptake of a hydrophilic test liquid, e.g., synthetic urine, is measured for a foam sample of known dimensions and capillary suction specific surface area. Such a procedure is described in greater detail in the TEST METHODS section hereinafter.

For purposes of the present invention, a particular foam material is considered to be substantially hydrophobic if, in the substantial absence of any added or residual surfactants or other hydrophilizing agents, it exhibits an adhesion tension of less than about 15 dynes/cm as determined by capillary suction uptake of synthetic urine having a surface tension of 65±5 dynes/cm. Conversely, a polymeric foam material is considered to be relatively hydrophilic when it exhibits an adhesion tension of 15 dynes/cm or greater, preferably 20 dynes/cm or greater, as determined by capillary suction uptake of this same synthetic urine.

In a first step of the method herein, a substantially hydrophobic polymeric foam is treated so as to incorporate into the foam material both a certain type of surfactant and a solution comprising a particular type of hydrophilizing agent which is dissolved in a suitable solvent. The surfactant which is incorporated into the foam material can comprise any substantially water-insoluble, mild, relatively non-irritating surfactant compound which tends to enhance the wettability of the polymeric surfaces with which it is contacted and onto which it may be deposited. Such surfactants can include, for example, sorbitan fatty acid esters, polyglycerol fatty acid esters and polyoxyethylene (POE) fatty acids and esters. Examples of surfactants of these types include TRIODAN®20 which is a commercially available polyglycerol ester marketed by Grindsted and EMSORB®2502 which is a sorbitan sesquioleate marketed by Henkel.

Especially preferred are the sorbitan fatty acid esters such as sorbitan monolaurate (SPAN®20), sorbitan monooleate (SPAN®80) and combinations of sorbitan trioleate (SPAN®85) and sorbitan monooleate (SPAN®80). One such particularly preferred surfactant combination comprises the combination of sorbitan monooleate and sorbitan trioleate in a weight ratio greater than or equal to about 3:1, more preferably greater than about 4:1.

Another particularly preferred sorbitan fatty acid ester is, as indicated, sorbitan monolaurate (SPAN®20). Sorbitan monolaurate is, in fact, so beneficial in imparting hydrophilicity characteristics to absorbant foams that its use as a hydrophilizing agent is the subject of the separate, concurrently filed U.S. Pat. application of DesMarais and Stone, having Ser. No. 07/743,838, which application is incorporated herein by reference. This sorbitan monolaurate material is accordingly highly preferred for use as the surfactant material to be incorporated into the foams herein in the context of the present invention.

The surfactant materials of the foregoing type can be incorporated into the foam materials herein by any suitable means which will result in the surfactant(s) contacting the polymeric surfaces of the foam material. Most preferably, this can be brought about by employing the surfactant material(s) as a component in the process which is used to prepare the foam materials herein. For the preferred foams herein which are prepared by polymerizing water-in-oil emulsions, the substantially water-insoluble surfactant materials can be added as emulsifiers to the monomer-containing oil phase of such emulsions. In this manner, the surfactant materials perform the dual role of stabilizing the emulsions to be polymerized and acting as residual hydrophilizing agents which contact and preferably coat the polymeric surfaces of the foam structure after this structure is formed. Surfactant materials can be added to the polymerizable monomer-containing oil phase to the extent of from about 0.5% to 20% by weight of the polymerizable monomer materials in the oil phase.

Alternatively, the surfactant materials used in the present invention can be introduced or reintroduced into the foam material which contains no surfactant as made or from which residual surfactants have been removed. Such introduction or reintroduction of surfactant can be carried out by treating such foams with an appropriate surfactant solution or suspension. Thus, the water-insoluble surfactants useful herein can be dissolved or dispersed in a suitable solvent or carrier such as isopropanol, and the resulting solution or suspension can be contacted with the foam material to be treated therewith. In this manner, the surfactant materials can be incorporated into the interstices of the foam structure.

The surfactant materials used in the present invention are generally incorporated into foam materials in amounts which, in conjunction with the hydrophilizing agent salt component, impart suitable hydrophilicity characteristics to the foams so treated. Frequently such amounts of incorporated surfactant will range from about 0.5% to 20% by weight of the polymerized foam material, more preferably from about 1% to 16% by weight of the polymeric foam material.

As indicated, the first step of the method of the present invention also involves the incorporation into the foam materials herein of a certain type of hydrophilizing agent salt solution. The essential component of such a hydrophilizing agent salt solution is a hydrophilizing agent salt which is selected from the toxicologically acceptable, hydrated or hydratable calcium and magnesium salts.

Nonlimiting examples of the hydrophilizing agent salts useful herein include hydrated and hydratable material s such as the following: calcium tartrate tetrahydrate; calcium thiosulfate hexahydrate; calcium chloride hexahydrate; calcium chloride tetrahydrate; calcium citrate tetrahydrate; calcium bromide trihydrate; calcium bromide hexahydrate; calcium sulfate dihydrate; magnesium orthophosphate octahydrate; magnesium tartrate pentahydrate; magnesium chloride hexahydrate; magnesium citrate pentahydrate; magnesium iodide octahydrate; magnesium sulfate heptahydrate; and magnesium salicylate tetrahydrate. Preferred hydrophilizing agents herein include hygroscopic or deliquescent salts such as the following: calcium chloride, calcium bromide, magnesium chloride and magnesium iodide. Mixtures of these salts may also be employed.

The calcium and magnesium salts used in the present invention should, of course, be toxicologically acceptable. Toxicologically acceptable salts are those which present little or no risk to humans or animals if they are accidentally ingested or inhaled in amounts which might be encountered during use or manufacture or after disposal of the hydrophilized foams herein. Thus, for example, hydrated magnesium arsenate might very well provide foams of suitable hydrophilicity. This salt, however, is toxic if ingested or inhaled and would therefore not be encompassed within the scope of the present invention.

The hydrophilizing agent salts as hereinbefore described will generally be dissolved in a suitable solvent to form a solution which can be incorporated into the polymeric foam material to be treated in accordance with the method herein. Water is the preferred solvent for use in preparing this treating solution, but various alcohol or water/alcohol solvents can also be employed. The hydrophilizing agent can be incorporated into the solution at any convenient concentration. Typically, solutions containing from about 1% to 10% by weight of solution of the hydrophilizing agent are used, but higher concentrations, and even saturated solutions, can be employed. When calcium chloride is used as the hydrophilizing agent, it is generally employed in aqueous solution at a concentration of from about 1% to 5% by weight.

As with the surfactant, the solution containing the hydrophilizing agent salt can be incorporated into the structure of the substantially hydrophobic polymeric foam material by any convenient procedure which will result in the solution filling a significant number of the cells within the foam. Most preferably, this can be brought about by actually employing the hydrophilizing agent solution in the process which is used to prepare the foam structure. Thus, for example, an appropriate calcium and/or magnesium salt may be added to the water phase of a water-in-oil emulsion which is to be used to prepare the polymeric foam. When such an emulsion is subsequently polymerized, the solid cellular structure of the foam will be formed around residual water phase material having the desired hydrophilizing agent salt dissolved therein.

Alternatively, foams made without any hydrophilizing agent solution used in their preparation process may, after formation, be treated by repeated contact and washing with an appropriate solution of hydrophilizing agent salt to thereby incorporate the solution into the foam. Such treatment of foam materials which are substantially hydrophobic as formed may be difficult, however, because hydrophilizing agent solutions, which are frequently aqueous, may not be readily absorbed into hydrophobic foams. In such instances, it may be necessary to force hydrophilizing agent solution into the foam structure by application of pressure or by means of repeated washing and/or foam squeezing steps. It may also be necessary, for example in the case of relatively large cell (>90μ) hydrophobic foams such as polyurethanes, to employ an alcohol or water/alcohol solvent for the hydrophilizing agent in order to realize acceptably uniform distribution of the hydrophilizing agent salt within the foam structure.

It is, of course, possible to employ a combination of the foregoing techniques for incorporating hydrophilizing agent salt solution into the foam structure being treated. Thus, for example, a portion of the eventually desired hydrophilizing agent salt may be incorporated into the process liquids used in the preparation of the foam. After formation of such a foam, additional or replacement hydrophilizing agent salt may be incorporated during subsequent post-formation treatment, e.g., washing, of the foam with hydrophilizing agent solution.

In a second process step of the method herein, the polymeric foam material, with its incorporated surfactant and incorporated solution of hydrophilizing agent salt, is subjected to drying procedures to remove therefrom solvent from the hydrophilizing agent salt solution. Drying can be effected by air, heat, or microwave treatment or by other conventional methods which serve to remove the solvent, but not excessive amounts of the hydrophilizing agent salt itself, from the foam structure.

It would be possible in accordance with this invention to completely remove from the foam solvent which has been used to deliver the hydrophilizing agent salt into the foam. Such complete removal of the solvent by the drying step would leave fine particles of the hydrophilizing agent salt deposited onto the foam surfaces. It will be appreciated from the discussion hereinafter that foam treated in this manner might be described as "over-dried" because, upon complete drying, the hydrophilizing agent salt loses its waters of hydration. Accordingly, the resulting foam appears to be hydrophobic. However, in the presence of relative humidities above about 40%, the hydrophilic surface of such completely dried foam will be restored. More preferably, the foam should not be dried completely to such a state. Rather, the drying conditions will preferably be adjusted such that the hydrophilizing agent salt retains its waters of hydration, and, as such, the resulting foam is hydrophilic as-made. Frequently, solvent will be removed from the foam structures treated by the method herein such that residual solvent, e.g., free water, in the foam comprises no more than about 50% by weight of the (dry) foam, more preferably no more than about 10% by weight of the (dry) foam.

It will be appreciated that the amount of hydrophilizing agent salt introduced throughout the foam network and onto the surfaces of the network structure of the foam via the instant method can vary, according to the degree of hydrophilization desired and according to the effectiveness of the hydrophilizing agent salt chosen. For example, with truly deliquescent hydrophilizing agent salts, a smaller proportion may be needed for satisfactory results. With salt materials that form lower hydrates, somewhat more of the hydrophilizing agent salt may have to be used. In general, the object of the present invention is to incorporate a hydrophilizing amount of the surfactant and the calcium and/or magnesium salt(s) into and onto the foam structure. For purposes of this invention, such an amount can be defined as that quantity of surfactant and of calcium and/or magnesium salt(s) which, when the salts are fully hydrated, provides a foam that exhibits an adhesion tension of at least about 15 dynes/cm, preferably at least about 20 dynes/cm, as determined by the capillary suction uptake at 37° C. of synthetic urine having a surface tension of 65±dynes/cm.

Typically, the dried foam will comprise at least about 0.05% by weight of the surfactant plus the hydrophilizing agent salt. When using materials such as calcium chloride, the foams will generally contain from about 0.1% to 7% by weight of the hydrophilizing agent salt based on the weight of the foam material. Higher levels can be used, but it should be appreciated that excessive amounts of the hydrophilizing agent salt will not, in general, serve any useful purpose and may cause the resulting foam to shed dusty particles due to an overloading of the dried hydrophilizing agent salt.

It will be appreciated that for the surfactant and the hydrophilizing agent salt to be effective in imparting hydrophilic characteristics to the foam being treated therewith, both the surfactant and the hydrophilizing agent salt must be substantially uniformly distributed within the internal structure of the foam. If the surfactant and/or the hydrophilizing agent salt is deposited within the foam only in discrete discontinuous zones, such as may happen for example if the surfactant or hydrophilizing agent salt solution forms beads or droplets within the foam structure formed by the polymeric struts, then the full foam hydrophilization effect provided by the method herein may not be realized.

Treatment of polymeric foam materials in accordance with the method of the present invention renders such foam materials suitable for absorbing hydrophilic liquids. While not limited by theory, it appears that the surfactant and the specific hydrophilizing agent salts used herein, in fact, do not chemically interact with the foam polymer material. Rather, it appears that the hydrophilizing agent salts herein function by simply providing molecules of water of hydration uniformly distributed at the surface of the foam. As noted, foams treated with the hydrophilizing agent salts herein can be "overdried" by removing water of hydration from the salts in the foam. Such overdried foams will then appear to be hydrophobic. However, such foams can be placed in a high humidity environment for a reasonably short period of time, whereupon their hydrophilic character can be considerably restored.

In environments wherein the foams herein are to be used, particularly in sanitary pads, diapers, and the like, the humidity close to the body or in contact with the skin is nearly 100%. Foams treated in accordance with the method herein with hydrated or hydratable hydrophilizing agent salts retain (or have restored) their hydrophilic character in the presence of the water. Thus, in-use, the hydratable salts can fully hydrate or rehydrate, either because of humidity in the air or because of the humidity provided by the close proximity with the body. In this manner, suitable hydrophilic foams useful for absorbing aqueous body fluids can be provided. Whatever the mechanism, the hydrated or hydratable hydrophilizing agent salts herein, in combination with the surfactant component, function in the desired manner to provide such hydrophilic foams without certain of the disadvantages hereinabove mentioned with regard to other means for hydrophilizing otherwise hydrophobic foams.

The hydrophilized foam materials of the present invention are especially useful as absorbents for aqueous body fluids in absorbent articles such as diapers, incontinence pads, catamenial products, and the like. The hydrophilic character of such treated absorbent foams permits such materials to readily accept body fluids such as urine and menses into their foam structures. Hydrophilized foam materials will in general exhibit desirable fluid transport, e.g., wicking, properties for aqueous fluids such as body fluids so that absorbed liquid can be moved within the material from one region of the absorbent foam to another.

The rate at which a polymeric foam material will wick, and especially vertically wick, aqueous fluid can, in fact, be used as a screening test to measure the extent to which a given polymeric foam material has been rendered hydrophilic. Vertical wicking rate can be determined by measuring the length of time which a test strip of foam of specified size takes to wick a colored test fluid such as synthetic urine up a specified vertical distance (e.g., 5 cm for foams that will wick fluid that far). Such a method for determining Vertical Wicking Rate is set forth in greater detail hereinafter in the TEST METHODS section.

An even simpler screening test useful for determining relative hydrophilicity of treated foam samples involves measurement of foam sample sink time. In such a test, foam samples are dropped into a beaker of aqueous test fluid, e.g., synthetic urine, and the amount of time taken for the samples to sink is recorded. Shorter sink times are observed for samples of greater hydrophilicity. A typical sink time test is described in greater detail hereinafter in the TEST METHODS section.

TEST METHODS

In describing the present invention, certain characteristics of absorbent foam materials are set forth. Where reported, these characteristics can be determined using the following test fluids and test methods.

I) Test Fluids and Foam Sample Preparation

A) Test Fluid—Synthetic Urine

Several of the measurements described in the tests herein involve the use of a test fluid such as synthetic urine or ethanol. The synthetic urine utilized in the tests described hereinafter is made from a commercially available synthetic urine preparation manufactured by Jayco Pharmaceuticals (Mechanicsburg, PA, 17055). This Jayco synthetic urine made from the preparation comprises KCl, 0.2%; $Na_2SO_4$, 0.2% $NH_4H_2PO_4$, 0.085%; $(NH_4)_2HPO_4$, 0.015%; $CaCl_2*2H_2O$, 0.025%; and $MgCl_2*6H_2O$, 0.05%. (weight %'s) The synthetic urine samples are prepared according to the label instructions using distilled water. To aid dissolution, the Jayco salt mixture is slowly added to the water. The sample is filtered if necessary to remove any particulates. Any unused synthetic urine is discarded after one week. To improve visibility of the fluid, 5 drops of blue food color can be added per liter of synthetic urine solution. The Jayco synthetic urine utilized has a surface tension of $65\pm5$ dynes/cm.

B) Foam Sample Preparation

The following Adhesion Tension and Vertical Wicking Rate tests involve the preparation and testing of foam samples of a particular specified size. These foam samples of the requisite size should be cut from larger blocks of foam using a sharp reciprocating knife saw. Use of this or equivalent type of foam cutting device serves to substantially eliminate foam sample edge flaws which could have adverse impact on certain of the measurements made in carrying out the test procedures hereinafter set forth.

Sample size specification also includes a dimension for foam sample caliper or thickness. Caliper or thickness measurements for purposes of the present invention should be made when the foam sample is under a confining pressure of 0.05 psi (350 Pa).

II) Adhesion Tension Determination

The adhesion tension exhibited by hydrophilized foam samples which imbibe test fluids via capillary suction is the product of the surface tension, $\gamma$, of the test fluid times the cosine of the contact angle, $\theta$, exhibited by the test fluid in contact with the interior surfaces of the foam sample. Adhesion tension can be determined experimentally by measuring the equilibrium weight uptake by capillary suction exhibited by two test samples of the same foam using two different test liquids. In the first step of such a procedure, specific surface area of the foam sample is determined using ethanol as the test fluid. The specific surface area so determined is then used as one factor in experimentally determining adhesion tension by measuring capillary suction uptake of a second test fluid, synthetic urine.

A) Specific Surface Area Measurements

Capillary Suction Specific surface area of the foam absorbents employed in the invention herein can be determined from the equilibrium weight uptake of a test liquid of known low surface tension. In this instance, absolute ethanol (flash point is 10° C.) is used.

To conduct the test, a tared foam sample strip of suitable dimensions (e.g., 25 cm long $\times$ 2 cm wide $\times$ 0.8 cm thick) is equilibrated at 22°$\pm$2° C., is positioned vertically and at one end is immersed 1-2 mm into a reservoir of the ethanol using a lab jack. The ethanol is allowed to wick up the foam strip to its equilibrium height which should be less than the sample length. The ethanol-containing strip is then weighed while still touching the reservoir to determine the weight of total ethanol uptake. During this procedure the sample should be shielded to prevent ethanol evaporation.

Specific surface area of the foam sample can be calculated from the following formula:

$$S_c = \frac{M_e G L_n}{M_n \gamma_e}$$

where $S_c$=capillary suction specific surface area in cm$^2$gm; $M_e$=mass of liquid uptake of EtOH in gms; G=the gravitational constant which is 980 cm/sec$^2$; $L_n$=total length of sample in cm; $M_n$=mass of dry foam sample in gm; and $\gamma_e$=surface tension of EtOH which is 22.3 dynes/cm.

B) Adhesion Tension Measurements

The capillary suction uptake procedure used as described to determine specific surface area of the foam sample is then repeated on other samples of the same foam in identical manner to the ethanol procedure except that JAYCO synthetic urine is used as the test fluid and the test is carried out at 37° C. Contact angle of the synthetic urine can then be calculated as follows from the known specific surface area and the synthetic urine uptake data:

$$\cos\theta_U = \frac{M_U G L_N}{M_N \gamma_U S_c}$$

where $\theta_U$=contact angle of Jayco synthetic urine in degrees; $M_U$=mass of liquid uptake of Jayco synthetic urine in gms; G=gravitational constant which is 980 cm/sec$^2$; $M_N$=mass of dry foam sample in gm; $\gamma_U$=surface tension of JAYCO urine which is ~65 dynes/cm; $S_c$=specific surface area of the foam sample in cm$^2$/gm as determined by the ethanol uptake procedure; and $L_n$=length of the foam sample in cm.

When a surfactant is present (for example, residual emulsifier on the foam sample surfaces and/or in the advancing test liquid), characterization of the advancing liquid front is defined by applying the adhesion tension (AT) equation:

$$AT = \frac{M_T G L_N}{M_N S_c}$$

wherein $M_T$ is the mass of the test liquid taken up by the foam sample, and G, $L_N$, $M_N$, and $S_c$ are as hereinbefore defined. [See Hodgson and Berg, *J. Coll. Int. Sci.*, 121(1), 1988, pp 22–31]

In determining adhesion tension for any given test liquid, no assumption is made of the numerical value of the surface tension at any point in time so that possible changes in surfactant concentration on the sample surfaces and/or in the advancing liquid during wicking are immaterial. The experimental value of adhesion tension ($\gamma\cos\theta$) is especially useful when viewed as a percentage of the maximum adhesion tension which is the surface tension of the test liquid (e.g., the maximum adhesion tension using JAYCO synthetic urine would be [65$\pm$5] [cos 0°]=65$\pm$5 dynes/cm).

III) Vertical Wicking Rate Determination

Vertical wicking rate is a measure of the ability of a dry foam to wick fluid vertically from a reservoir. The time required for the fluid front to wick through a 5 cm vertical length of a strip of foam can be measured to give a vertical wicking rate, at least for foams that have equilibrium vertical wicking heights greater than 5 cm.

Jayco synthetic urine colored with blue food coloring is used in the following method to determine vertical wicking rate. In this test procedure, the materials are equilibrated at 22° C., and the test is performed at the same temperature.

1) Sample Preparation i) A strip of foam approximately 25 cm$\times$2 cm$\times$0.8 cm is prepared as in the Adhesion Tension test hereinbefore described.

ii) A fluid reservoir is placed on top of a lab jack and the foam sample is clamped at one end so that it is suspended vertically over the fluid reservoir.

iii) A ruler is clamped next to the foam sample so that the bottom (0 cm) of the ruler is about 1-2 mm above the bottom of the foam sample.

iv) The fluid reservoir is filled about ¾ full with the dyed synthetic urine solution.

2) Vertical Wicking Rate i) The reservoir is raised up to the bottom of the foam sample with the lab jack. A timer is started as soon as the fluid touches the bottom of the foam sample.

ii) The reservoir is immediately raised until the liquid just touches the bottom of the ruler. The lab jack may need to be adjusted to keep 1-2 mm of the sample immersed, and the sample should be shielded to prevent evaporation.

iii) The time it takes the fluid front to reach 5 cm is recorded. For comparison purposes the times for the fluid test to reach 2 cm and 10 cm are also recorded if the foam sample has wicking characteristics such that the test fluid will wick that far.

IV. Sink Time Determination

Cylindrical foam samples 1.125 inches (2.86 cm) in diameter of any suitable thickness (e.g., 0.8 cm) are cut from larger foam pieces. The cylindrical samples are dropped from a height of 2-3 inches (5-7.6 cm) into a 250 mL beaker containing approximately 100 mL of Jayco synthetic urine in such a way that the fl at cylindrical surface contacts the test fluid in the beaker. A stopwatch timer i s started as soon as the bottom of the foam sample contacts the test fluid. The sample is observed until the test fluid wicks to the top surface of the sample. When the top face of the foam sample is substantially wetted out, the timer is stopped, and the sink time is recorded.

Temperature of the test fluid can affect sink time significantly, especially for the preferred water-in-oil based foams of the present invention. Thus the test fluid should be maintained at the same temperature for all samples being comparatively tested in a particular sink time screening exercise. Test fluid "cold" temperatures of about 70°–80° F. (21°–27° C.) and test fluid "hot" temperatures of about 110°–120° F. (43°–49° C.) are frequently employed.

EXAMPLES

Preparation of hydrophilized absorbent foam materials, the characteristics of such hydrophilized foam materials and utilization of these hydrophobic foam absorbents in a disposable diaper are all illustrated by the following examples.

EXAMPLE I

Preparation of a hydrophilized foam absorbent on a semi-pilot plant scale is illustrated by this example.

Emulsion Preparation

Calcium chloride (320 g.) and potassium persulfate (48 g.) are dissolved in 32 liters of distilled water. This provides the water phase used to form a high internal phase emulsion.

To a monomer combination comprising styrene (900 g.), divinylbenzene (1260 g.) and 2-ethylhexylacrylate (3840 g.) are added sorbitan monooleate (960 g. as SPAN®80) and sorbitan trioleate (240 g. as SPAN®85). After mixing, this comprises the oil phase used in the formation of the high internal phase emulsion.

At temperatures in the range of 55° C. to 65° C., separate streams of the oil phase and water phase are fed to a dynamic mixing chamber. Thorough mixing of the combined streams in the dynamic mixing chamber is achieved by means of a pin impeller. At this scale of operation, an appropriate pin impeller comprises a cylindrical shaft of about 22 cm. in length with a diameter of about 1.9 cm. The shaft holds two rows of 17 and two rows of 16 cylindrical pins each having a diameter of 0.5 cm. extending radially outward from the central axis of the shaft to a length of 1.6 cm. The four rows are positioned at 90° angles around the circumference of the impeller shaft. The rows that are perpendicular to each other are offset along the length of the shaft such that no pins which are perpendicular to each other are in the same radial plane extending from the axis of the shaft. The pin impeller is mounted in a cylindrical sleeve which forms the dynamic mixing chamber, and the pins in the impeller have a clearance of 0.8 mm from the walls of the cylindrical sleeve. The impeller is operated at a speed of 800 revolutions per minute.

A static mixer (14 inches long by ½ inch outside diameter by 0.43 inch inside diameter) is mounted further downstream from the dynamic mixing chamber to help provide some back pressure. This helps keep the dynamic mixing chamber comprising the cylindrical sleeve with its pin impeller full. This also helps to ensure appropriate and complete mixing of the oil and water phases.

An emulsion having the requisite ratio of water to oil phases is approached gradually. At first, flow rates are adjusted so that 3 parts by weight of the water phase and 1 part by weight of the oil phase enter the dynamic mixing chamber with the pin impeller at an oil phase flow rate of 0.75 g/sec (0.1 pounds/minute). The water to oil phase ratio is increased, over a period of a few minutes, until a ratio of 29 parts water phase to 1 part oil phase is passing into the dynamic mixing chamber, at a rate of 23 ml/sec. Visually, the emulsion at this stage flows from the static mixer orifice with the consistency of a whipping cream and "sets" to a consistency reminiscent of a creamy yogurt.

Polymerization of the Emulsion

At this point, the emulsion emerging from the static mixer is ready for curing. The emulsion is fed to a generally rectangular mold which is made of polyethylene and which has the dimensions, 38 cm length; 25 cm width and 22 cm depth. Emulsion is emptied into such molds until each mold contains approximately 20,000 ml of the emulsion to be cured.

Curing is effected by placing the emulsion-containing molds in a curing oven at a temperature of 60° C. for a period of about 16 hours. After curing, the resulting solid polymerized foam material contains up to 98% water and is soft and sopping wet to the touch.

Foam Washing and Hydrophilization

The wet cured foam material is removed from the curing mold and subjected to further processing. The residual water phase in the foam is expressed by applying sufficient pressure to the foam material, or to thin slices of the foam material, to squeeze out at least 90% of the retained original residual water phase material.

The foam sample is then washed for 20 seconds in 60° C. water containing calcium chloride as a hydrophilizing agent salt. Such a hydrophilizing solution contains 1% by weight of calcium chloride.

The calcium chloride solution used in the first washing is again expressed using pressure, and the foam is then treated with a second washing with the calcium chloride solution at 60° C. This second rinse is intended to leave a residue of both emulsifier/surfactant (16% by weight) and calcium chloride in the foam, thereby rendering the internal foam surfaces relatively hydrophilic.

Foam Dewatering

The twice hydrophilized foam is then again pressed to express excess hydrophilizing solution from within its porous structure. The foam material is then dried by subjecting it to oven drying for 12 hours at 60° C. After drying the foam material is cut into sample pieces suitable for the Vertical Wicking Rate testing as hereinafter described.

EXAMPLE II

Another polymeric foam material is prepared in the same general manner as set forth hereinbefore in Example I. In this example, the emulsion preparation, polymerization, washing, hydrophilization and drying procedures are carried out as in Example I except that a 10% $CaCl_2$ solution (3200 g $CaCl_2$) is used as the water phase.

EXAMPLE III

In this example, polymeric foam materials prepared according to the general procedures of Examples I and II are tested for their propensity to vertically wick synthetic urine. Comparative foam materials, which are subjected to different washing procedures to thereby remove or replace the $CaCl_2$ hydrophilizing agent salt, are also tested.

All of the foam samples are prepared and tested for vertical wicking rate and Sink Time in the manner hereinbefore described in the TEST METHODS section. Descriptions of the foam samples, the foam washing treatment solutions and the Vertical Wicking Rates and Sink Times exhibited by these foam samples are set forth in Table I.

TABLE I
VERTICAL WICKING RATES

| Foam Type: | Example I ($CaCl_2$) | Example I ($H_2O$ only)[a] | Example I ($FeSO_4 \cdot 7H_2O$)[b] | Example I ($CuCl_2$)[c] |
| --- | --- | --- | --- | --- |
| Wicking Time To: (Min:Sec) | | | | |
| 2 cm | 0:28 | 4:44 | >60:00 | 12:37 |
| 5 cm | 1:56 | 8:33 | — | >60:00 |
| 10 cm | 12:43 | >60:00 | — | — |
| Sink Time (sec) at 22° | 29 | 159 | >360 | >360 |

| Foam Type: | Example II ($CaCl_2$) | Example II ($H_2O$ only)[x] | Example II ($MgCl_2$)[y] |
| --- | --- | --- | --- |
| Wicking Time (Min:Sec) To: | | | |
| 2 cm | 0:48 | — | 0:15 |
| 5 cm | 2:42 | 10:10 | 1:17 |
| 10 cm | 9:23 | 21:36 | 8:39 |
| Sink Time (sec) at 22° | 6 | 308 | 4 |

[a]Example I foam washed with 60° C. tap water containing no added salt
[b]Example I foam washed with 60° C. tap water containing 2% $FeSO_4 \cdot 7H_2O$
[c]Example I foam washed with 60° C. tap water containing 1% $CuCl_2$
[x]Example II foam washed with 60° C. tap water containing no added salt
[y]Example II foam washed with 60° C. tap water containing 1% $MgCl_2$ The Table III data show that both $CaCl_2$ and $MgCl_2$ treatments of the Examples I and II foam materials provide desirably high vertical wicking rates and desirably short sink times. Treatments with water alone or with other hydrated or hydratable salts, on the other hand, are much less effective at rendering foam hydrophilic as demonstrated by the relatively lower vertical wicking rates and relatively longer sink times exhibited by the foams so treated.

EXAMPLE IV

The foam of Example II is prepared and hydrophilized using 10% aqueous solutions of the following salts, respectively: $CaCl_2:MgCl_2$ (1:1 wt. mixture); $MgSO_4$; and $MgI_2$.

EXAMPLE V

A polyurethane foam is prepared in the conventional manner using toluene diisocyanate and polyether polyol. The foam is repeatedly soaked and squeezed in a 10% solution of $CaCl_2$ and sorbitan monooleate/sorbitan trioleate in isopropanol. The excess solution is expressed using hand pressure. The foam is allowed to air-dry and is thus hydrophilized by virtue of the residual surfactant and $CaCl_2$ remaining therein.

EXAMPLE VI

Figure 2:
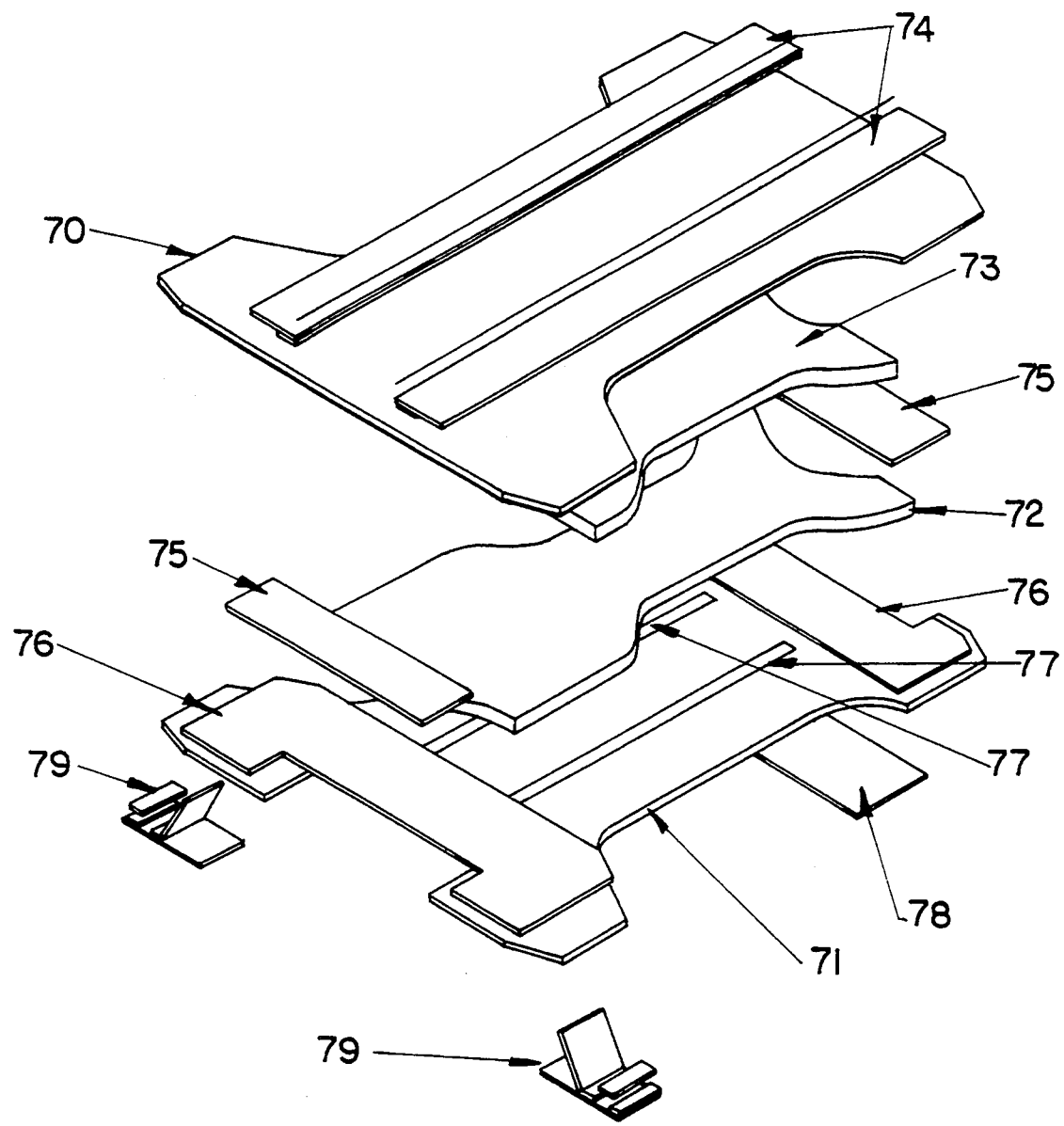
FIG. 2 of the drawings represents a blown-apart view of the components of a diaper structure which has a dual layer absorbent core configuration and which employs a hydrophilized absorbent foam material as one of its elements.

A disposable baby diaper using a foam absorbent which has been hydrophilized according to this invention is prepared as follows using the configuration and components shown in the expanded and blown-apart depiction of FIG. 2. Such a diaper comprises a thermally bonded polypropylene topsheet, 70, a fluid-impervious polyethylene backing sheet, 71, and a dual layer absorbent core positioned between the topsheet and the backing sheet. The dual layer absorbent core comprises a modified hourglass-shaped, fluid storage/redistribution layer, 72, comprising a hydrophilized absorbent foam of the Example I type positioned below a modified-hourglass shaped fluid acquisition/distribution layer, 73. The topsheet contains two substantially parallel barrier leg cuff strips, 74, with elastic. Affixed to the diaper backsheet are two rectangular elasticized waistband members, 75. A1 so affixed to each end of the polyethylene backsheet are two waistshield elements, 76, constructed of polyethylene. A1 so affixed to the backsheet are two parallel leg elastic strips, 77. A sheet of polyethylene, 78, is affixed to the outside of the backsheet as a dedicated fastening surface for two pieces, 79, of Y type which can be used to fasten the diaper around the wearer.

The acquisition/distribution layer of the diaper core comprises a 92%/8% wetlaid mixture of stiffened, twisted, curled cellulosic fibers and conventional non-stiffened cellulosic fibers. The stiffened, twisted, curled cellulosic fibers are made from sourthen softwood kraft pulp (Foley fluff) which has been cross-linked with glutaraldehyde to the extent of about 2.5 mole percent on a dry fiber cellulose anhydroglucose basis. The fibers are crosslinked according to the "dry crosslinking process" as described in Dean, Moore, Owens and Schoggen; U.S. Pat. No. 4,822,453; Issued Apr. 18, 1989, incorporated herein by reference.

These stiffened fibers are similar to the fibers having the characteristics described as follows in Table II.

Table II

Stiffened, Twisted, Curled Cellulose (STCC) Fibers

Type=Southern softwood kraft pulp crosslinked with
glutaraldehyde to the extent of 1.41 mole percent on a dry
fiber cellulose anhydroglucose basis
Twist Count Dry=6.8 nodes/mm
Twist Count Wet=5.1 nodes/mm
Isopropol Alcohol Retention Value=24%
Water Retention Value=37%
Curl Factor=0.63

The conventional non-stiffened cellulose fibers used in combination with the STCC fibers are also made from Foley fluff. These non-stiffened cellulose fibers are refined to about 200 CSF (Canadian Standard Freeness).

The acquisition/distribution layer has an average dry density of about 0.07 g/cm$^3$, an average density upon saturation with synthetic urine, dry weight basis, of about 0.08 g/cm$^3$, and an average basis weight of about 0.03 g/cm$^2$. About 9.2 grams of the fluid acquisition/distribution layer are used in the diaper core. The surface area of the acquisition/distribution layer is about 46.8 in$^2$ (302 cm$^2$). It has a caliper of about 0.44 cm.

The fluid storage/redistribution layer of the diaper core comprises a modified hourglass-shaped piece of a hydrophilized absorbent foam of the type described hereinbefore in Example I. About 12 grams of this foam are used to form this storage/redistribution layer which has a surface area of about 65.9 in$^2$ (425 cm$^2$) and a caliper of about 0.325 in (0.826 cm).

A diaper having this particular core configuration exhibits especially desirable and efficient utilization of the core for holding discharged urine and accordingly provides exceptionally low incidence of leakage when worn by an infant in the normal manner.

EXAMPLE VII

A lightweight pantiliner suitable for use between menstrual periods comprises a hydrophilized foam pad according to Example II (surface area 117 cm$^2$; thickness 1.5 mm), said pad being interposed between a porous formed-film topsheet according to Ahr et. al.; U.S. Pat. No. 4,463,045; Issued Jul. 31, 1984 and a backsheet which comprises a 0.03 mm thickness polyethylene film.

EXAMPLE VIII

A sanitary napkin is prepared according to Example VII, but employs a 4 mm thick hydrophilized foam pad according to Example I and a porous nonglossy formed film topsheet. The sanitary napkin has the configuration described in Van Tilburg; U.S. Pat. No. 4,687,478; Issued Aug. 18, 1987.

EXAMPLE IX

This example illustrates the preparation of another type of surfactant/CaCl$_2$-hydrophilized HIPE foam material falling within the scope of the present invention.

Emulsion Preparation

Calcium chloride (36.32 kg) and potassium persulfate (568 g) are dissolved in 378 liters of water. This provides the water phase stream to be used in a continuous process for forming a polymerizable High Internal Phase Emulsion (HIPE).

To a monomer combination comprising styrene (1600 g), divinylbenzene 55% technical grade (1600 g), and 2-ethylhexylacrylate (4800 g) is added sorbitan monolaurate (960 g as SPAN ®20). After mixing, this combination of materials is allowed to settle overnight. The supernatant is withdrawn and used as the oil phase in a continuous process for forming a polymerizable HIPE emulsion. (About 75 g of a sticky residue is discarded.)

At an aqueous phase temperature of 48°–50° C. and an oil phase temperature of 22° C., separate streams of the oil phase and water phase are fed to a dynamic mixing apparatus. Thorough mixing of the combined streams in the dynamic mixing apparatus is achieved by means of a pin impeller. At this scale of operation, an appropriate pin impeller comprises a cylindrical shaft of about 21.6 cm in length with a diameter of about 1.9 cm. The shaft, as described in Example I, holds 4 rows of pins, 2 rows having 17 pins and 2 rows having 16 pins, each having a diameter of 0.5 cm extending outwardly from the central axis of the shaft to a length of 1.6 cm. The pin impeller is mounted in a cylindrical sleeve which forms the dynamic mixing apparatus, and the pins have a clearance of 0.8 mm from the walls of the cylindrical sleeve.

A spiral static mixer is mounted downstream from the dynamic mixing apparatus to provide back pressure in the dynamic mixer and to provide improved incorporation of components into the emulsion that is eventually formed. Such a static mixer is 14 inches (35.6 cm) long with a 0.5 inch (1.3 cm) outside diameter. The static mixer is a TAH Industries Model 070-821, modified by cutting off 2.4 inches (6.1 cm).

The combined mixing apparatus set-up is filled with oil phase and water phase at a ratio of 2 parts water to 1 part oil. The dynamic mixing apparatus is vented to allow air to escape while filling the apparatus completely. The flow rates during filling are 1.127 g/sec oil phase and 2.19 cm$^3$/sec water phase$^3$/sec water phase.

Once the apparatus set-up is filled, agitation is begun in the dynamic mixer, with the impeller turning at 1800 RPM. The flow rate of the water phase is then steadily increased to a rate of 35.56 cm$^3$/sec over a time period of 130 sec. The back pressure created by the dynamic and static mixers at this point is 7.5 PSI (51.75 kPa). The impeller speed is then steadily decreased to a speed of 1200 RPM over a period of 60 sec. The back pressure drops to 4.5 PSI (31.05 kPa). At this point, the impeller speed is instantly increased to 1800 RPM. The system back pressure remains constant thereafter at 4.5 PSI (31.05 kPa).

Polymerization of the Emulsion

The formed emulsion flowing from the static mixer at this point is collected in Rubbermaid Economy Cold Food Storage Boxes, Model 3500. These boxes are constructed of food grade polyethylene and have nominal dimensions of 18"×26"×9" (45.7 cm×66 cm 22.9 cm). The true inside dimensions of these boxes are pretreated with a film of a solution comprising a 20% solution of SPAN ®20 in an equal weight solvent mixture of xylene and isopropanol. The solvent mixture is allowed to evaporate to leave only the SPAN ®20. Forty-seven liters of emulsion are collected in each box.

The emulsion-containing boxes are kept in a room maintained at 65° C. for 18 hours to bring about polymerization of the emulsion in the boxes to thereby form polymeric foam material.

Foam Washing, Hydrophilization and Dewatering

After curing is complete, the wet cured foam material is removed from the curing boxes. The foam at this point contains about 30–40 times the weight of polymerized material (30–40X) of the residual water phase containing dissolved emulsifiers, electrolyte and initiator. The foam material is sliced with a sharp reciprocating saw blade into sheets which are 0.350 inches (0.89 cm) in caliper. These sheets are then subjected to compression in a series of 3 nip rolls which gradually reduce the residual water phase content of the foam to about 6 times (6X) the weight of the polymerized material. At this point, the sheets are then resaturated with a 1% CaCl$_2$ solution at 60° C., are squeezed in a nip to a water phase content of about 10X, resaturated with the 1% CaCl$_2$ solution at 60° C., and then squeezed again in a nip to a water phase content of about 10X.

The foam sheets, which now contain about 10X of what is essentially a 1% CaCl$_2$ solution are passed through a final nip equipped with a vacuum slot. The last nip reduces the CaCl$_2$ solution content to about 5 times (5X) the weight of polymer. The foam remains compressed after the final nip at a caliper of about 0.080 in. (0.2 cm). The foam is then dried in an air circulating oven set at about 60° C. for about three hours. Such drying reduces the moisture content to about 5–7% by weight of polymerized material. At this point, the foam sheets have a caliper of about 0.075 in. (0.19 cm) and are very drapeable. The foam also contains about 5% by weight (anhydrous basis) of residual hydrated calcium chloride as a hydrophilizing agent along with about 11% by weight of residual sorbitan monolaurate (SML). In the collapsed state, the density of the foam is about 0.17 g/cm$^3$. When expanded to its free absorbent capacity (26.5 ml/g) in JAYCO synthetic urine, the expanded foam has a capillary suction specific surface area of about 2.24 m$^2$/g, a pore volume of about 29.5 cc/g and an average cell size of about 15 microns.

The SML/CaCl$_2$-hydrophilized foam sheets prepared as in Example IX represent a preferred "thin-until-wet" embodiment of the present invention inasmuch as these hydrophilized foam sheets are in the form of collapsed foam material which will expand upon contact with aqueous body fluids. Once expanded, the foam materials are useful for absorbing the body fluids that have caused the foam to expand. Such preferred collapsed foams are those which are formed from a non-hydrolyzed polymeric material, which have a capillary suction specific surface area of from about 0.5 to 5.0 m$^2$/g, which contain from about 0.5% to 20% of residual emulsifier, and which contain from about 0.1% to 7% by weight (anhydrous basis) of the foam material of a toxicologically acceptable, hygroscopic, hydrated salt, which is preferably calcium chloride or magnesium chloride, as a hydrophilizing agent salt.

In its collapsed state, such hydrophilized foam material will have a residual water content of from about 4% to 15% by weight of polymerized material when it is stored at ambient conditions of 72° F. (22° C.) and 50% relative humidity. This water content includes both water of hydration associated with the hygroscopic, hydrated salt as well as free water absorbed within the foam. Such collapsed hydrophilized foam material will also have a dry basis density ranging from about 0.08 to 0.3 g/cm$^3$.

In its expanded state, such preferred thin-until-wet SML/-CaCl$_2$-hydrophilized foam materials will have a pore volume from about 12 to 100 ml/g and will exhibit a resistance to compression deflection such that a confining pressure of 5.1 kPa produces after 15 minutes of strain from about 5% to 95% compression of the structure when it is saturated at 37° C. to its free absorbent capacity with synthetic urine having a surface tension of 65±5 dynes/cm. The average cell size of these preferred thin-until-wet hydrophilized foam materials in the expanded state will range from about 5 to 30 microns. The dry basis density of the expanded hydrophilized foam material upon saturation to its free absorbent capacity in this synthetic urine will range from about 9% to 28% of its dry basis density in the collapsed state.

EXAMPLE X

A foam material prepared in general as in Example IX is tested for its hydrophilicity characteristics using the Sink Time procedure described in the TEST METHODS section. Such a foam material is also subjected to various treatment procedures to lo remove added or residual hydrophilizing agents therefrom and to selectively reintroduce certain materials to test their effectiveness at imparting hydrophilicity characteristics to the foam material.

The foam material, treating agents and sink time test results are set forth hereinafter in Table III.

TABLE III

| EXAMPLE IX TYPE FOAM | CaCl$_2$ wt-% | SML[1] wt-% | Sink Time in JAYCO Synthetic Urine | |
|---|---|---|---|---|
| | | | Cold (~21–27° C.) | Hot (~43–49° C.) |
| As-made | 3.7% | 11% | 70 sec | 3 sec |
| Water washed | | | | |
| Expanded Form | -0- | 11% | >20 min | 4 sec |
| Collapsed Form | -0- | 11% | 300 sec | 2 sec |
| CaCl$_2$ re-treated (from H$_2$O) | 3.6% | 11% | 180 sec | 3 sec |
| IPA[2] washed | -0- | -0- | *Floated indefinitely* | |
| CaCl$_2$ re-treated (from IPA) | ~5% | -0- | Floated for hrs | Floated >15 min |
| SML re-treated (from IPA) | -0- | 11% | ~5 sec | ~1 sec |
| SMO/STO$_3$ re-treated (from IPA) | -0- | 19% | ~300 sec | ~180 sec |

[1]SML = Sorbitan monolaurate (SPAN ® 20)
[2]IPA = Isopropanol
[3]SMO/STO = Sorbitan monooleate (SPAN ® 80) and sorbitan trioleate (SPAN ® 85) in a 4:1 weight ratio The Table I (Example III) and the Table III data considered together show that the combination of CaCl$_2$ and surfactant incorporated into foam samples of the Examples I, II and IX types provides foams having hydrophilicity characteristics which are in general superior to those having either no incorporated hydrophilizing agents at all or CaCl$_2$ or surfactant alone.

EXAMPLE XI

A diaper substantially similar in configuration to that described in Example IV is prepared using as the fluid storage/redistribution layer a sheet of thin-until-wet collapsed SML/CaCl$_2$-hydrophilized absorbent foam of the type described in Example IX. In such a diaper, the fluid acquisition/distribution layer, comprising the stiffened, twisted, curled cellulosic fibers, is used in an amount of about 13 grams. The thin-until-wet, SML/CaCl$_2$-hydrophilized fluid storage/redistribution layer is also used in an amount of about 13 grams.

A diaper having this particular configuration exhibits especially desirable and efficient utilization of the absorbent core for holding discharged urine and accordingly provides exceptionally low incidence of leakage when worn by an infant in the normal manner.

I claim:

1. A method for rendering substantially hydrophobic polymeric foam material suitable for absorbing hydrophilic liquids, which method comprises A) incorporating into a substantially hydrophobic polymeric foam material a substantially water-insoluble surfactant selected from the group consisting of sorbitan fatty acid esters, polyglycerol fatty acid esters and polyoxyethylene fatty acids and esters polyglycerol fatty acid esters and polyoxyethylene fatty acids and esters and a hydrophilizing salt solution formed from a solvent and a dissolved hydrophilizing salt selected from the group consisting of toxicologically acceptable, hydrated or hydratable calcium and magnesium slats; and B) thereafter drying said polymeric foam material to remove solvent therefrom and to thereby leave incorporated within said polymeric foam material a hydrophilizing amount of said surfactant and said hydrophilizing salt.

2. A method according to claim 1 wherein the solvent used to form the hydrolizing salt solution is selected from the group consisting of water, isopropanol and mixtures thereof.

3. A method according to claim 2 wherein the hydrophilizing salt is selected from the group consisting of calcium halides, magnesium halides and mixtures thereof.

4. A method according to claim 3 wherein the polymeric foam material is an open-celled foam.

5. A method according to claim 4 wherein the total amount of surfactant and hydrophilizing agent salt left incorporated within the foam material comprises at least about 0.05% by weight of the foam material.

6. A method according to claim 5 wherein the polymeric foam material is dried to the extent that it contains no more than about 50% by weight of the foam of free water.

7. A method according to claim 6 wherein the polymeric foam material is a polyurethane foam.

8. A method according to claim 6 wherein the polymeric foam material is a polymerized water-in-oil emulsion foam.

9. A method according to claim 8 wherein the polymeric foam material is formed from polymerized monomers selected from the group consisting of styrene, alkyl(meth)acrylates, divinylbenzene and combinations of these monomers.

10. A method for rendering substantially hydrophobic polymeric foam material suitable for absorbing hydrophilic liquids, which method comprises A) incorporating an aqueous solution containing from about 1% to 10% by weight of calcium chloride in water into a polymeric foam material prepared by polymerizing a water-in-oil emulsion containing polymerizable monomers and from about 0.5% to 20% by weight of the polymerizable monomers of a surfactant selected from the group consisting of sorbitan monolaurate and mixtures of sorbitan monooleate and sorbitan trioleate in the oil phase of said emulsion; and B) thereafter drying said polymeric foam material to remove water therefrom and to leave incorporated within said foam material at least about 0.05% by weight of said foam material of surfactant plus calcium chloride and no more than about 50% by weight of said foam material of free water.

11. A method according to claim 10 wherein

A) the aqueous solution incorporated into the polymeric foam material contains from about 1% to 5% by weight calcium chloride;

B) the dried polymeric foam material contains from about 0.1% to 7% by weight of said foam material of calcium chloride; and C) the dried polymeric foam material contains no more than about 10% by weight of said foam material of free water.

12. A method according to claim 11 wherein the polymerizable monomers in the oil phase of the water-in-oil emulsion used to form the polymeric foam material are selected from the group consisting of styrene, alkyl(meth)acrylates, divinylbenzene and combinations of these monomers.

13. A hydrophilized polymeric foam material suitable for absorbing hydrophilic liquids, said hydrophilized polymeric foam material comprising a substantially hydrophobic polymeric foam material; a hydrophilizing amount of at least about 0.05% by weight of said polymeric foam material of the combination of a substantially water-insoluble surfactant selected from the group consisting of sorbitan fatty acid esters, polyglycerol fatty acid esters and polyoxyethylene fatty acids and esters and a hydrophilizing salt selected from the group consisting of toxicologically acceptable, hydrated or hydratable calcium and magnesium salts, incorporated into aid polymeric foam material; and no more than about 50% by weight of said polymeric foam material of free water incorporated within said polymeric foam material.

14. A hydrophilized polymeric foam material according to claim 13 wherein the polymeric foam material is an open-celled foam.

15. A hydrophilized polymeric foam material according to claim 14 wherein the hydrophilizing agent salt is selected from the group consisting of calcium halides, magnesium halides and mixtures thereof.

16. A hydrophilized polymeric foam material according to claim 15 wherein the amount of surfactant incorporated within the foam material ranges from about 0.5% to 20% by weight of the foam material; the amount of hydrophilizing agent salt incorporated within the foam material ranges from about 0.1% to 7% by weight of the foam material; the amount of free water incorporated within the polymeric foam material comprises no more than about 10% by weight of said foam material; and the hydrophilizing agent salts are fully hydrated.

17. A hydrophilized polymeric foam material according to claim 16 wherein the polymeric foam material is a polyurethane-type foam.

18. A hydrophilized polymeric foam according to claim 16 wherein the polymeric foam material is a polymerized water-in-oil emulsion foam.

19. A hydrophilized polymeric foam material according to claim 18 wherein the polymeric foam material is formed from polymerized monomers selected from the group consisting of styrene, alkyl(meth)acrylates, divinylbenzene and combinations of these monomers.

20. A hydrophilized polymeric foam material according to claim 19 wherein the surfactant is selected from the group consisting of sorbitan monolaurate and mixtures of sorbitan monooleate and sorbitan trioleate and the hydrophilizing salt is calcium chloride.

* * * * *